(12) United States Patent
Chen et al.

(10) Patent No.: US 10,788,349 B2
(45) Date of Patent: Sep. 29, 2020

(54) EXPERIMENTAL SYSTEM AND METHOD FOR IN-SITU SIMULATING DIFFERENT FLOODING-DRYING FREQUENCIES OF SHORE ZONES

(71) Applicant: NANJING HYDRAULIC RESEARCH INSTITUTE, Nanjing (CN)

(72) Inventors: Qiuwen Chen, Nanjing (CN); Wenqing Shi, Nanjing (CN); Haoyu Zhu, Nanjing (CN); Dongsheng Liu, Nanjing (CN); Yuchen Chen, Nanjing (CN); Honghai Ma, Nanjing (CN); Qi Zhang, Nanjing (CN); Yingxin Hong, Nanjing (CN)

(73) Assignee: NANJING HYDRAULIC RESEARCH INSTITUTE, Nanjing (CN)

( * ) Notice: Subject to any disclaimer, the term of this patent is extended or adjusted under 35 U.S.C. 154(b) by 3 days.

(21) Appl. No.: 16/724,203

(22) Filed: Dec. 21, 2019

(65) Prior Publication Data
US 2020/0124460 A1    Apr. 23, 2020

(51) Int. Cl.
| G01F 23/00 | (2006.01) |
| G01C 13/00 | (2006.01) |
| G01N 33/24 | (2006.01) |

(52) U.S. Cl.
CPC ....... *G01F 23/0061* (2013.01); *G01C 13/002* (2013.01); *G01N 33/24* (2013.01)

(58) Field of Classification Search
CPC .... G01F 23/0061; G01C 13/002; G01N 33/24
See application file for complete search history.

(56) References Cited

U.S. PATENT DOCUMENTS

| 2012/0150783 A1* | 6/2012 | Jung | ............. | G06N 20/00 |
| | | | | 706/46 |
| 2016/0047099 A1* | 2/2016 | Zhang | ............. | G06Q 10/04 |
| | | | | 703/9 |

* cited by examiner

*Primary Examiner* — John E Breene
*Assistant Examiner* — L. Anderson
(74) *Attorney, Agent, or Firm* — CBM Patent Consulting, LLC

(57) ABSTRACT

An experimental system comprises a water level indicator, a data processing module, and an experimental simulator. The water level indicator is connected to the data processing module, and the water level indicator is mounted nearby the experimental simulator when in use. The experimental simulator comprises several experimental units. Each experimental unit comprises a first pipe, a second pipe, and a third pipe, wherein the first pipe perpendicularly communicates with the second pipe, a check valve which allows water to flow out but allows no water to flow in is connected to the water outlet of the second pipe, and the third pipe perpendicularly communicates with the second pipe and is parallel to the first pipe. The heights of the third pipes of the several experimental units are in a decreasing or increasing order.

9 Claims, 3 Drawing Sheets

EXPERIMENTAL SYSTEM AND METHOD FOR IN-SITU SIMULATING DIFFERENT FLOODING-DRYING FREQUENCIES OF SHORE ZONES

This application claims priority to Chinese Patent Application Ser. No. 201910948606.0 filed 8 Oct. 2019.

FIELD OF THE INVENTION

The present invention relates to the field of environmental monitoring for shore zones, and in particular to an experimental system and method for in-situ simulating different flooding-drying frequencies of shore zones.

BACKGROUND OF THE INVENTION

The shore zone of a lake or reservoir is a hot spot of various biogeochemical reactions. Exploring the physicochemical properties of sediments in different flooding periods and the biogeochemical reactions inside the sediments during the wet-dry process of the shore zone is a basis for revealing the mechanism of biogeochemical reactions in the shore zone. Disturbances caused by environmental differences between different areas and between time scales must be avoided or controlled to accurately study the biogeochemical reaction mechanism of the shore zone. At present, most of experiments on biogeochemical reactions of sediments under wet-dry cycles in shore zones have focused on aspects such as indoor culture experiment, field isotopic tracing or field long-term monitoring. There are often great differences between the indoor culture experiment results and the real results, because the field situations cannot be exactly simulated. The field isotopic tracing experiment and the field long-term monitoring cannot avoid the environmental differences on a time scale to perform the quantitative simulation of different floods during the same period, or cannot avoid the difference of sediments to perform the simulation of different floods in the same experimental site.

SUMMARY OF THE INVENTION

Objective of the invention: In order to reduce disturbances caused by the nonhomogeneity of sediments and other factors, the present invention provides an experimental system and method for in-situ simulating different flooding-drying frequencies of shore zones, which can simulate wet-dry in different cycles under the same environment in the field, and have the advantages of field simulation, enabling comparative experiments in the same period and at the same place, requiring for no manual monitoring, etc.

Technical solution: The experimental system for in-situ simulating different flooding-drying frequencies of undercurrent areas of shore zones described in the present invention comprises a water level indicator, a data processing module, and an experimental simulator. The water level indicator is connected to the data processing module, and the water level indicator is mounted nearby the experimental simulator when in use. The experimental simulator comprises several experimental units. Each experimental unit comprises a first pipe, a second pipe, and a third pipe, wherein the height of the first pipe is about 150 cm, the first pipe perpendicularly communicates with the second pipe, a check valve which allows water to flow out but allows no water to flow in is connected to the water outlet of the second pipe, and the third pipe perpendicularly communicates with the second pipe and is parallel to the first pipe. The heights of the third pipes of the several experimental units are in a decreasing or increasing order. The data processing module is configured to generate flooding-drying data according to the water level of the experimental simulator monitored by the water level indicator.

Further, the position where the first pipe and the second pipe of each experimental unit communicate with each other is located approximately at the lower third of the first pipe. The heights of the first pipes of all the experimental units of the experimental simulator are equal, and the heights of all the third pipes are less than the height of the first pipe.

Alternatively, the water level indicator and the data processing module are integrated together to form a whole.

Alternatively, the water level indicator and the data processing module are two devices, and are connected to each other through a wired network or a wireless network.

Further, the data processing module is configured specifically to calculate the flooded condition of each experimental unit according to a water level monitored by the water level indicator, the known elevation of the water outlet of the second pipe of each experimental unit and the height of the third pipe of each experimental unit, and to generate flooding frequencies, as well as time and duration of each flood.

The experimental method for in-situ simulating different flooding-drying frequencies of undercurrent areas of shore zones described in the present invention is based on the above experimental system, and the method comprises:

along the direction of water flow, the experimental units of the experimental simulator being mounted at approximately equal intervals in undercurrent areas of a shore zone of a lake or reservoir flooded by an annual average water level, wherein the heights of the third pipes of all the experimental units are in an increasing or decreasing order, and the first pipe of each experimental unit is inserted vertically into the sediment of the shore zone until the second pipe is in contact with the sediment of the shore zone;

the water level indicator being mounted nearby the experimental simulator;

after being mounted, the water level indicator automatically monitoring the water level of each experimental unit of the experimental simulator and sending the water level information to the data processing module; and the data processing module calculating the flooded condition of each experimental unit according to a water level monitored by the water level indicator, the known elevation of the water outlet of the second pipe of each experimental unit and the height of the third pipe of each experimental unit, and generating flooding frequencies, as well as time and duration of each flood.

The second pipe of each experimental unit is parallel to the shoreline and is oriented to the direction of water flow when the experimental simulator is mounted. The elevations of the mounting positions of all experimental units are approximately equal, and the elevations of the second pipes are equal.

Beneficial effects: The present invention has the following outstanding advantages in comparison with the prior art.

1. The disturbance of sediment heterogeneity is eliminated. The sediment is a carrier for biogeochemical reactions in a shore zone, and the present experimental system carries out an experiment in the same area, avoiding the influence of sediment heterogeneity on an experimental result.

2. The disturbance of environmental difference on a time scale is eliminated. In the past experimental methods, a long-term monitoring means was often adopted to avoid the disturbance of sediment heterogeneity, but the influence of other environmental factors could not be controlled on a long time scale. By utilizing the third pipes as water inlets and the second pipes as water outlets, the present experimental system can simulate different flood s through water inlets of different elevations to achieve the objective of quantitatively studying the relation between the dry-wet circulation cycle and the biogeochemical reaction of the sediment in the shore zone, thereby eliminating the disturbance of environmental factors on a time scale.

3. The experimental system and method is easy and flexible to be operated, and do not require long-term manual monitoring. A lot of time and labor can be saved since the experimental system is easy to be fabricated and mounted and flexible to be arranged, and does not require the long-term attendance of people in the field during a long-term simulation.

DETAILED DESCRIPTION OF THE INVENTION

Figure 1:
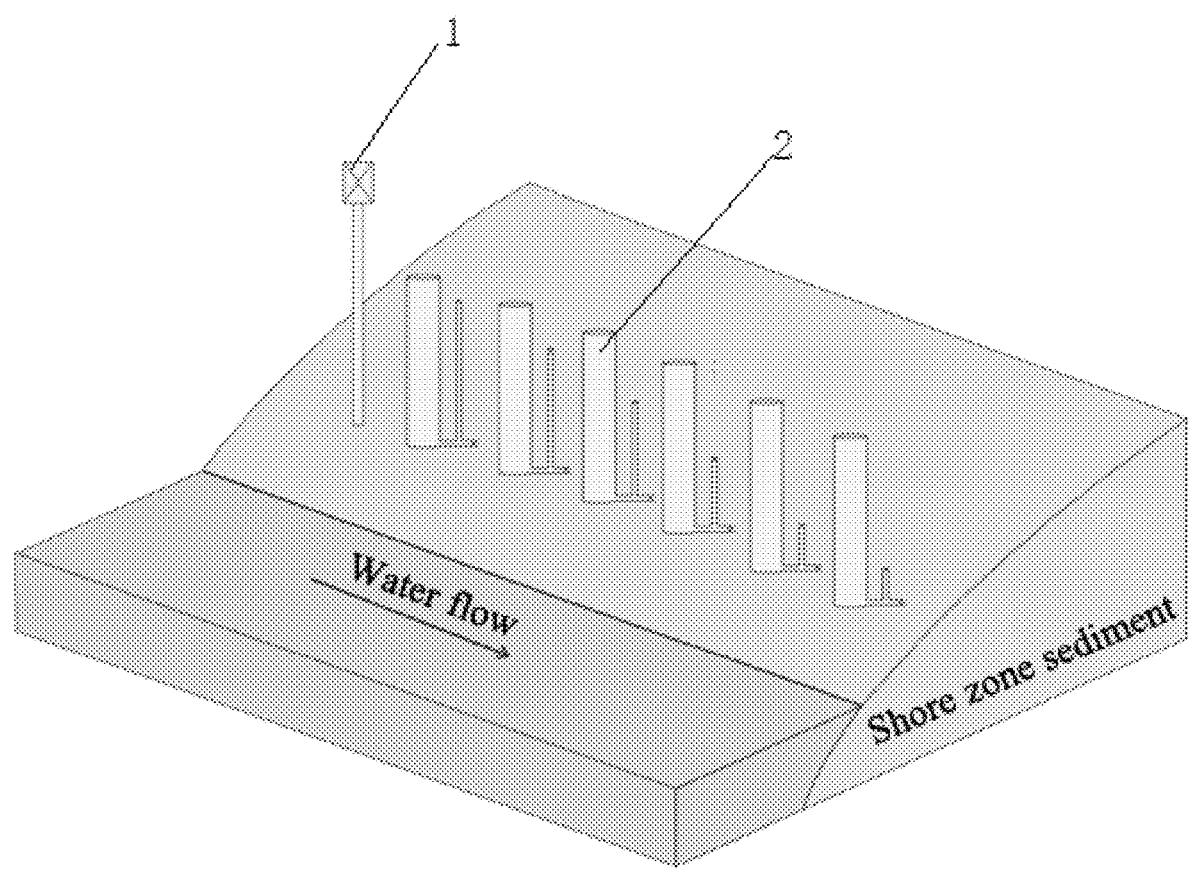
FIG. 1 is a mounting schematic diagram of an experimental system for in-situ simulating different flooding-drying frequencies of undercurrent areas of shore zones provided by the present invention.
Figure 2:
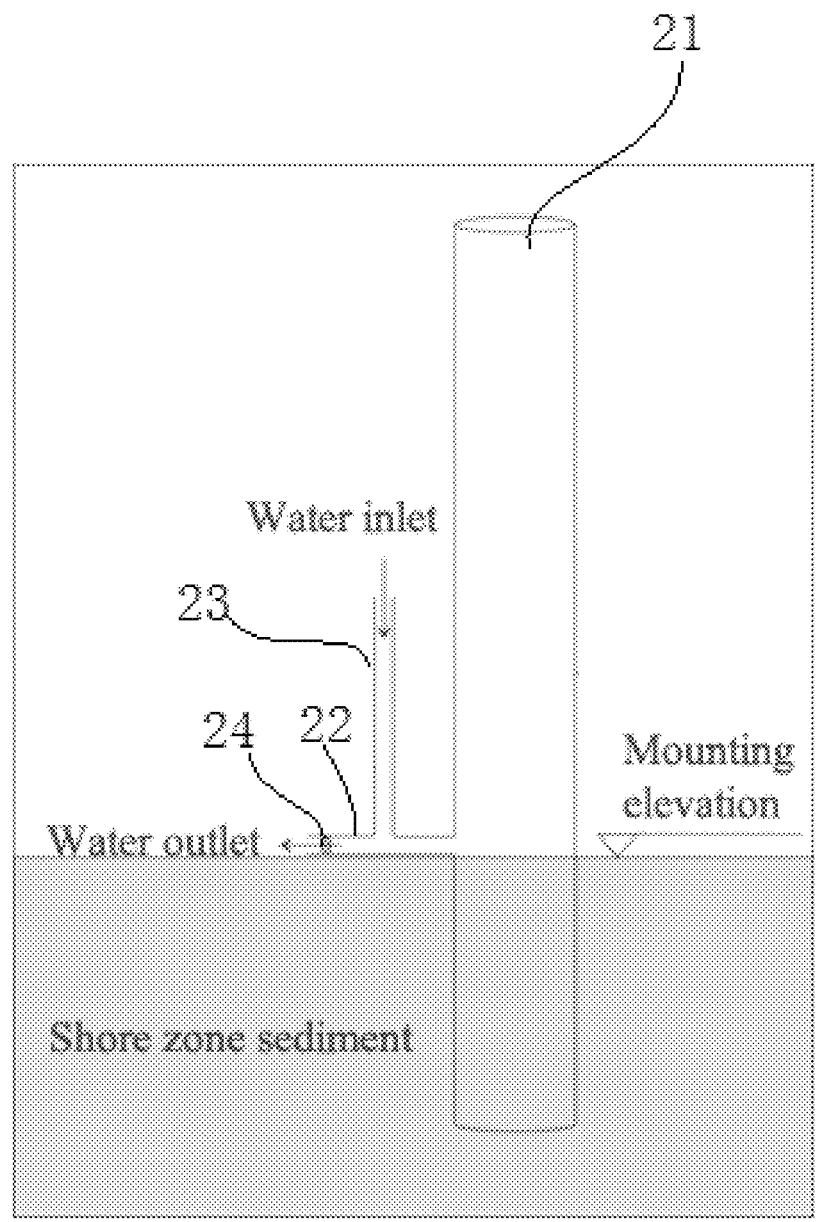
FIG. 2 is a structural diagram of an experimental unit in FIG. 1.

The present embodiment provides an experimental system for in-situ simulating different flooding-drying frequencies of undercurrent areas of shore zones. As shown in FIG. 1 and FIG. 2, the experimental system comprises a water level indicator 1, a data processing module, and an experimental simulator. The water level indicator 1 is connected to the data processing module. The experimental simulator comprises several experimental units 2. Each experimental unit 2 comprises a first pipe 21, a second pipe 22, and a third pipe 23, wherein the first pipe 21 and the second pipe 22 of the experimental unit 2 perpendicularly communicate with each other, the communicating position is located approximately at the lower third of the first pipe, a check valve 24 which allows water to flow out but allows no water to flow in is connected to the water outlet of the second pipe 22, and the third pipe 23 perpendicularly communicates with the second pipe 22 and is parallel to the first pipe 21. The heights of the first pipes 21 of all experimental units of the experimental simulator are equal, and the heights of all the third pipes 23 are less than the height of the first pipe 21. The heights of all the third pipes are in a decreasing or increasing order, with an increment or decrement generally greater than or equal to 5 cm. The parameters of all experimental units are the same except that the third pipes have different heights. The inlet of the third pipe 23 of each experimental unit serves as a water inlet, and the outlet of the second pipe serves as a water outlet.

The water level indicator 1 can be selected as required, and in the present embodiment, is a radar water level indicator. The water level indicator 1 is mounted nearby the experimental simulator, with a precision requirement of 1 cm to 2 cm, and a monitoring time interval of 2 h to 6 h. The data processing module is configured specifically to calculate the flooded condition of each experimental unit according to a water level monitored by the water level indicator, the known elevation of the water outlet of the second pipe of each experimental unit and the height of the third pipe of each experimental unit, and to generate flooding-drying frequencies, as well as time and duration of each flood, which can be implemented by a program such as MATLAB. The water level indicator 1 and the data processing module can be integrated together to form a whole. During monitoring, the data, via the data processing module, can be locally stored through an USB/SD card or can be sent to other devices through the network. The water level indicator and the data processing module can also be two devices, and are connected to each other through a wired network or a wireless network, and the data processing module is located ashore.

The usage and principle of the present invention are as follows: The experimental units are mounted nearby the sediment of the shore zone of a lake or reservoir flooded by an annual average water level; in order to avoid the influence of water flow and waves on the water drainage of the experimental simulator, the second pipes 22 should be parallel to the shoreline and oriented to the direction of water flow; the first pipes 21 are inserted vertically into the sediment of the shore zone until the bottoms of the second pipes 22 are in contact with the sediment; and the reason for inserting the first pipes 21 deep into the sediment of the shore zone is to prevent a lot of water in the lake or reservoir from rushing into the first pipes 21 when the water level rises. For each individual experimental unit, in a cycle of rise and fall of water level, when the water level rises but is lower than the elevations of the water inlets of the third pipes 23, the sediments in the first pipes 21 are always in a dried state; when the water level rises to be higher than the elevations of the water inlets of the third pipes 23, due to the principle of a communicating vessel, the water levels in the first pipes 21 are flushed with the outside water level, and the sediments are in a flooded state; when the water level falls to be lower than the elevations of the water inlets of the third pipes 23, the water levels in the first pipes 21 fall along with the water level of the reservoir; the water level continues to fall until the water level reaches the elevation of the water outlets of the second pipes 22, the sediments in the first pipes 21 are dried, and a complete flooding-drying cycle is complete when the next flooding starts. For the whole experimental simulator, when the water of the lake or reservoir starts to swell, the third pipes 23 with lower water inlets are flooded first, and the water enters the first pipes 21 from the water inlets to flood the sediments at the bottom; the interiors of the experimental units with higher water inlets are not flooded, and the sediments in the round pipes are in the dried state; when the water level falls but is higher than the water outlets of the second pipes 22, the flooded sediments continue to be flooded, and only when the water level is lower than the one-way water outlets of the second pipes 22, the water in the first pipes 21 is drained out completely, so that a drying period starts. The water level indicator 1 periodically detects and sends the water level of the lake or reservoir to the data processing module, and the data processing module processes the data to obtain the flooded condition of each experimental unit, and generates flooding frequencies, as well as time and duration of each flood. Thus, the effect of simulating different dry-wet circulation cycles in the same experimental area and during the same period of time to reduce the disturbance caused by the nonhomogeneity of the sediments can be achieved. In the whole experimental cycle, according to a specific experimental scheme, by assaying sediment samples collected from the first pipes of the experimental units in the lab, and based on the flooded condition of each experimental unit during each period, the objective of quantifying the relation between the wet-dry cycle and a biogeochemical reaction of the sediment in the shore zone is achieved ultimately.

The present embodiment also provides an experimental method for in-situ simulating different flooding-drying frequencies of undercurrent areas of shore zones, and the experimental method is based on the above experimental system and comprises the following steps.

(S1) along the direction of water flow, the experimental units of the experimental simulator were mounted at approximately equal intervals in undercurrent areas of a shore zone of a lake or reservoir flooded by an annual average water level, wherein the heights of the third pipes of all the experimental units were in an increasing or decreasing order, and the first pipe of each experimental unit was inserted vertically into the sediment of the shore zone until the second pipe was in contact with the sediment of the shore zone.

The annual average water level, annual average lowest water level and annual average highest water level of the lake that were selected in the present embodiment were 3.4 m, 3.0 m and 4.2 m respectively, and this experiment lasted for 6 months. The experimental simulator comprised eight experimental units, the first pipe 21 of each experimental unit was a seamless stainless steel round pipe with an internal diameter of 20 cm and a height of 150 cm, the second pipe and the third pipe were seamless stainless steel round pipes with an internal diameter of 3 cm, and the heights of the third pipes 23 were 5 cm, 15 cm, 25 cm, 35 cm, 45 cm, 55 cm, 65 cm and 75 cm respectively. The experimental simulator was mounted on the sediment of the lake shore zone having an elevation of 3.4 m. In order to avoid the influence of water flow and waves on the water drainage of the experimental simulator, the second pipes were parallel to the shoreline, and were oriented to the direction of water flow, and the second pipes of all experimental units were located at an elevation of 3.4 m and mounted at an interval of 10 cm.

(S2) the water level indicator was mounted nearby the experimental simulator. The automatic monitoring time interval of the water level indicator was set as 3 hours.

(S3) after being mounted, the water level indicator automatically monitored the water level of each experimental unit of the experimental simulator and sent the water level information to the data processing module.

(S4) the data processing module calculated the flooded condition of each experimental unit according to a water level monitored by the water level indicator, the known elevation of the water outlet of the second pipe of each experimental unit and the height of the third pipe of each experimental unit, and generated flooding-drying frequencies, as well as time and duration of each flood.

Figure 3:
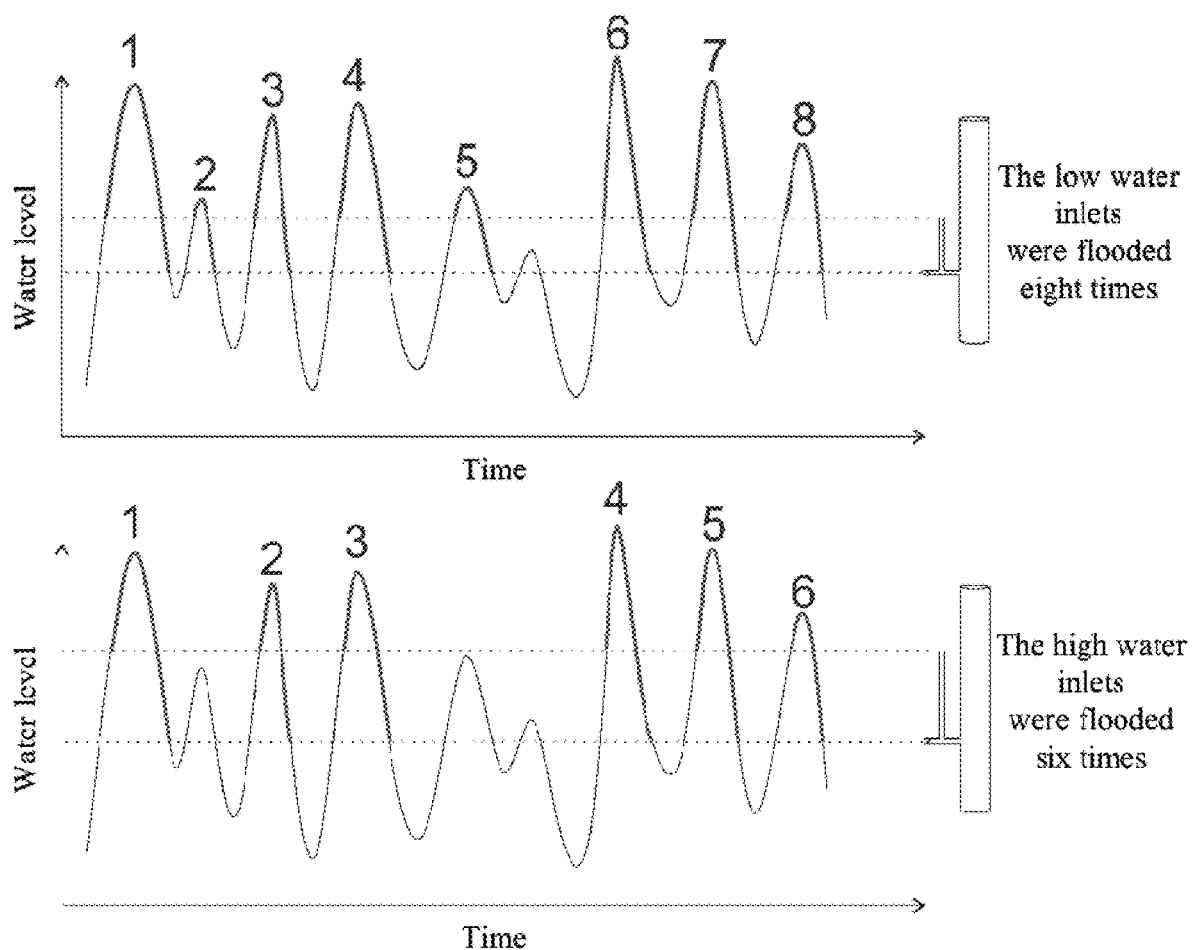
FIG. 3 is a comparison diagram for flooding frequencies of water inlets at different elevations obtained by adopting the present invention.

During a process of rise and fall of flood after the experimental simulator was mounted, the water level of the lake rose from 3.35 m to 3.7 m, and then fell back to 3.4 m. In this process, the lake water sequentially flooded the water inlets at elevations of 5 cm, 15 cm and 25 cm, and the sediments in the first pipes of these three experimental units were flooded; as the water level gradually fell, the water inlets were exposed one by one according to their elevations of 25 cm, 15 cm and 5 cm, the water levels in the round pipes slowly fell, and the water in the three first pipes was drained out completely when the water levels fell to 3.4 m. A flooding-drying cycle completed when the water level rose next time. In the whole cycle, only the sediments in the experimental units with the water inlets at elevations of 5 cm, 15 cm and 25 cm were flooded, and the sediments in the other experimental units were in the dried state. The data processing module calculated the flooded condition of each experimental unit according to the water level information, the known water outlet elevations and mounting elevations (3.4 m) of the eight experimental units, and could directly generate the number, time and duration of a flood of each experimental unit by the MATLAB self-compiled program. FIG. 3 shows a comparison diagram for flooding frequencies of the water inlets at different elevations, and the dark curves represent the periods of the sediments in the round pipes being flooded. The change of the mass of each nitration reactant of the sediments in the first pipes was then determined in the lab, the denitrification rate of the sediments within 6 months was calculated, and ultimately the objective of quantifying the relation between the dry-wet circulation cycles and the denitrification of the sediment in the shore zone was achieved based on the flooded condition of each experimental unit.

What is disclosed above is merely a preferred embodiment of the present invention rather than limits the scope of rights of the present invention, so all equivalent variations which will be made according to the claims of the present invention shall fall into the scope of the present invention.

What is claimed is:

1. An experimental system for in-situ simulating different flooding-drying frequencies of shore zones, comprising a water level indicator, a data processing module, and an experimental simulator, wherein the water level indicator is connected to the data processing module, the water level indicator is mounted nearby the experimental simulator when in use, the experimental simulator comprises several experimental units, each experimental unit comprises a first pipe, a second pipe, and a third pipe, the first pipe perpendicularly is connected to the second pipe, a check valve which allows water to flow out but allows no water to flow in is connected to the water outlet of the second pipe, the third pipe perpendicularly is connected to the second pipe and is parallel to the first pipe, the several experimental units are arranged by heights of their third pipes from largest to smallest or from smallest to largest: the water level indicator monitors water levels of the experimental simulator, data of the water levels are collected and calculated by the data processing module to generate flooding-drying data.

2. The experimental system for in-situ simulating different flooding-drying frequencies of shore zones according to claim 1, wherein the position where the first pipe and the second pipe of each experimental unit communicate with each other is located at the lower third of the first pipe.

3. The experimental system for in-situ simulating different flooding-drying frequencies of shore zones according to claim 1, wherein the heights of the first pipes of all experimental units of the experimental simulator are equal, and the height of any of the third pipes are shorter than the height of any of the first pipes.

4. The experimental system for in-situ simulating different flooding-drying frequencies of shore zones according to claim 1, wherein the water level indicator and the data processing module are integrated together to form a whole.

5. The experimental system for in-situ simulating different flooding-drying frequencies of shore zones according to claim 1, wherein the water level indicator and the data processing module are two devices, and are connected to each other through a wired network or a wireless network.

6. The experimental system for in-situ simulating different flooding-drying frequencies of shore zones according to claim 1, wherein the data processing module is configured specifically to calculate the flooded condition of each experimental unit according to a water level monitored by the water level indicator, the known elevation of the water outlet of the second pipe of each experimental unit and the height of the third pipe of each experimental unit, and to generate flooding frequencies, as well as time and duration of each flood.

7. An experimental method for in-situ simulating different flooding-drying frequencies of shore zones, wherein the method is based on the experimental system according to claim 1, and the method comprises:

along the direction of water flow, the experimental units of the experimental simulator being mounted at approximately equal intervals in a shore zone of a lake or reservoir flooded by an annual average water level, wherein all the experimental units are arranged by the heights of their third pipes from largest to smallest or from smallest to largest, and the first pipe of each experimental unit is inserted vertically into the sediment of the shore zone until the second pipe is in contact with the sediment of the shore zone;

the water level indicator being mounted nearby the experimental simulator;

after being mounted, the water level indicator automatically monitoring the water level of each experimental unit of the experimental simulator and sending the water level information to the data processing module; and the data processing module calculating the flooded condition of each experimental unit according to a water level monitored by the water level indicator, the known elevation of the water outlet of the second pipe of each experimental unit and the height of the third pipe of each experimental unit, and generating flooding frequencies, as well as time and duration of each flood.

8. The experimental method for in-situ simulating different flooding-drying frequencies of shore zones according to claim 7, wherein the second pipe of each experimental unit is parallel to the shoreline and is oriented to the direction of water flow when the experimental simulator is mounted.

9. The experimental method for in-situ simulating different flooding-drying frequencies of shore zones according to claim 7, wherein, when the experimental simulator is mounted, the elevations of the mounting positions for all experimental units are approximately equal, and the elevations of the second pipes are equal.

\* \* \* \* \*